United States Patent

Denzel et al.

[11] 4,012,373
[45] Mar. 15, 1977

[54] PYRAZOLO[3',4'-2,3]PYRIDO[4,5-e]b-BENZO-1,5-DIAZEPINONES

[75] Inventors: Theodor Denzel, Nurnberg; Hans Hoehn, Tegernheim; Ernst Schulze, Regensburg, all of Germany

[73] Assignee: E. R. Squibb & Sons, Inc., Princeton, N.J.

[22] Filed: Sept. 22, 1972

[21] Appl. No.: 291,503

[52] U.S. Cl. .................. 260/239.3 P; 424/263; 424/246; 424/248.5; 424/267; 424/248.57; 424/248.58; 260/310 R; 260/295.5 B
[51] Int. Cl.[2] .................................. C07D 471/14
[58] Field of Search .............................. 260/239.3 P

[56] References Cited
UNITED STATES PATENTS 3,420,818 1/1969 Ott .......................... 260/239.3 P

*Primary Examiner*—Henry R. Jiles
*Assistant Examiner*—Robert T. Bond
*Attorney, Agent, or Firm*—Lawrence S. Levinson; Merle J. Smith

[57] ABSTRACT

The new pyrazolo[3',4'-2,3]pyrido[4,5-e]b-benzo-1,5-diazepinone compounds having the general formula

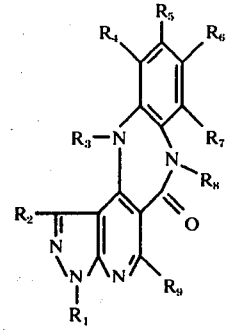

are useful as central nervous system depressants and anti-inflammatory agents. These compounds also increase the intracellular concentration of adenosine-3',-5'-cyclic monophosphate.

15 Claims, No Drawings

PYRAZOLO[3',4'-2,3]PYRIDO[4,5-e]b-BENZO-1,5-DIAZEPINONES

SUMMARY OF THE INVENTION

This invention relates to new pyrazolo[',4'-2,3]-pyrido [4,5-e]b-benzo-1,5-diazepinones. These new compounds have the general formula

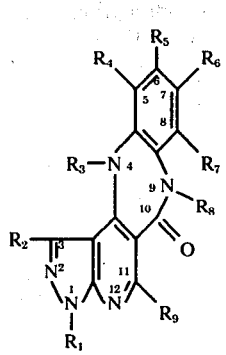

The symbols have the following meanings in formula I and throughout this specification: $R_1$ represents hydrogen, lower alkyl, phenyl, phenyl-lower alkyl or cyclo-lower alkyl, $R_2$ represents hydrogen, lower alkyl or phenyl, $R_3$ and $R_8$ each represents hydrogen, alkyl up to 10 carbons, preferably lower alkyl, phenyl-lower alkyl, cyclo-lower alkyl or an amino-alkylene group of the formula II

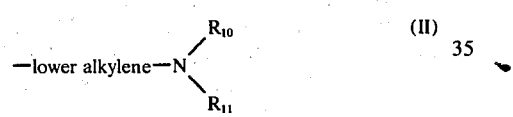

in which $R_{10}$, $R_{11}$ each is hydrogen, lower alkyl or hydroxy-lower alkyl. In addition, the nitrogen may be part of a heterocyclic of 5 or 6-members, in which an additional nitrogen, sulfur or oxygen is present, i.e., pyrrolidino, piperidino, morpholino or thiamorpholino. These heterocyclic groups may also bear a lower alkyl, lower alkoxy or hydroxy-lower alkyl group, for example 2,3 or 4-(lower alkoxy)piperidino, e.g., 2-methoxypiperidino, 2,3- or 4-(lower alkyl)piperidino, e.g., 2,3-or 4-methylpiperidino, (lower alkyl)pyrrolidino, e.g., 2-methylpyrrolidino, (lower alkoxy)pyrrolidino, e.g., 2-ethoxypyrrolidino (lower alkyl)morpholino, e.g., 3-methylmorpholino or 2-methylmorpholino, (lower alkoxy)morpholino, e.g., 2-ethoxymorpholino, (lower alkyl)thiamorpholino, e.g., 3-methylthiamorpholino or 2-methylthiamorpholino, (lower alkoxy)-thiamorpholino, e.g., 2-methoxythiamorpholino.

$R_4$, $R_5$, $R_6$ and $R_7$ each is hydrogen, halogen, lower alkyl or lower alkoxy. $R_9$ is hydrogen, lower alkyl or phenyl.

Preferred compounds of formula I are those wherein $R_1$ is hydrogen or lower alkyl, especially ethyl, $R_2$ is hydrogen or methyl, $R_3$ and $R_8$ each is hydrogen, lower alkyl or di(lower alkyl)amino-lower alkylene, especially ethyl- or dimethylaminopropyl, $R_4$, $R_5$, $R_6$, $R_7$ are hydrogen, halogen, especially chlorine, or lower alkoxy, especially methoxy, $R_9$ is hydrogen or lower alkyl, especially hydrogen.

DETAILED DESCRIPTION OF THE INVENTION

The various groups referred to above are of the following types: the lower alkyl and lower alkylene groups include straight or branched chain hydrocarbon groups of up to seven carbon atoms, like methyl, ethyl, propyl, isopropyl and the like, up to four carbon atom chains being preferred. The phenyl-lower alkyl and alkoxy contain similar radicals attached to a phenyl or oxygen, respectively. All four common halogens are included but chlorine and bromine are preferred. The cyclo-lower alkyl groups are the 3 to 6 carbon alicyclics cyclopropyl, cyclobutyl, cyclopentyl and cyclohexyl, especially the last two.

The compounds of formula I are produced by the following series of reactions. The symbols in the structural formulas have the same meaning as previously described.

A 5-aminopyrazole of the formula

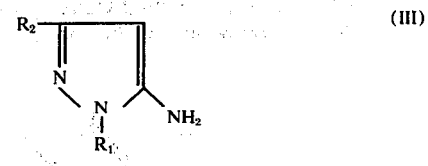

[produced analogous to the procedure described in Z.f. Chemie 10, 386 (1970)] is made to react with a compound of the formula

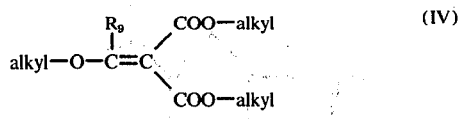

by heating at a temperature of about 120°–130° C.

The resulting compound of the formula

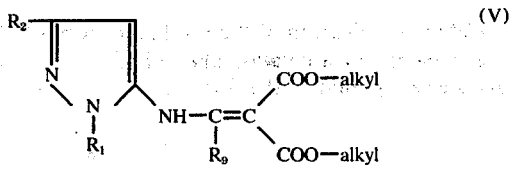

is cyclized in an inert organic solvent such as diphenyl ether at about 230° to about 260° C. while distilling off the alcohol formed, producing a compound of the formula

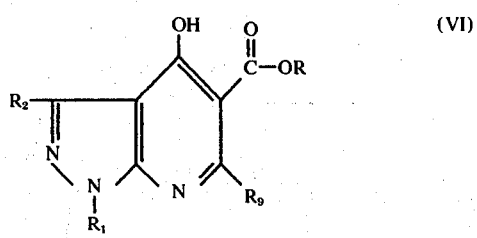

in which $R_1$, besides the alkyl groups, represents also the above mentioned groups. This 4-hydroxy compound is refluxed for several hours with a phosphorus halide like phosphorus oxychloride to obtain the intermediate of the formula

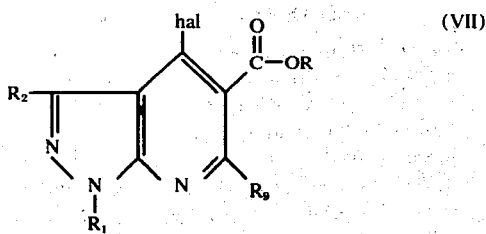

Alternatively, instead of cyclizing the compound of formula V in an inert organic solvent at about 230° to 260° C. as described above, this product also undergoes cyclization by treatment with phosphorus oxychloride producing directly the intermediate of formula VII.

This compound of formula VII is made to react with an appropriately substituted 2-nitroaniline in the presence of a base like sodium hydride, in a high boiling solvent like dioxane or diethyleneglycoldimethylether to produce a compound of the formula

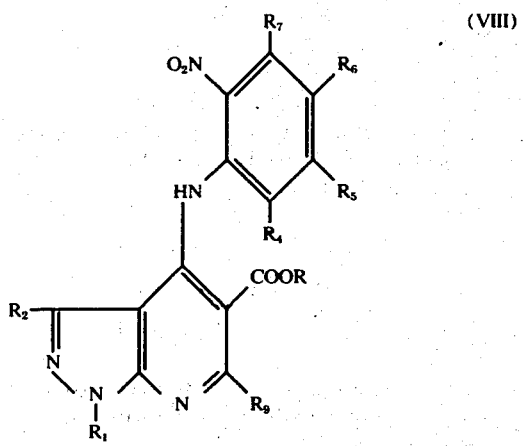

Catalytic reduction of the product of formula VIII in the presence of a catalyst like palladium on charcoal gives a compound of the formula

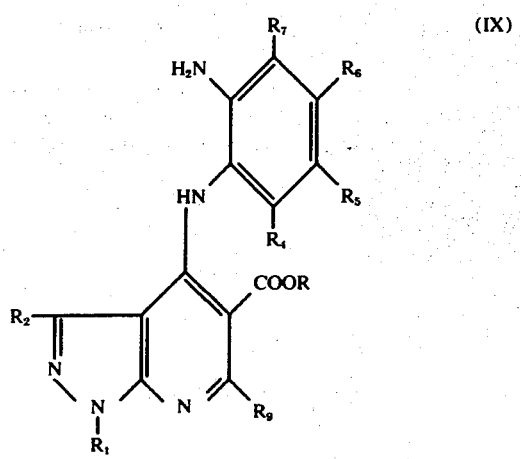

In the case when $R_4$, $R_5$, $R_6$ and $R_7$ are hydrogen, a compound of formula IX is directly produced by reacting o-phenylenediamine with the product of formula VII in the presence of potassium carbonate or triethylamine.

Treatment of the product of formula IX with a basic agent like potassium tert. butylate results in the formation of a compound of formula I wherein $R_3$ and $R_8$ are hydrogen.

Instead of employing potassium tert. butylate, the cyclization may also be effected by heating compounds of formula IX with a strong acid like polyphosphoric acid.

According to a modification of the cyclization step, a compound of formula IX is treated with an inorganic base like sodium hydroxide resulting in a compound of the formula

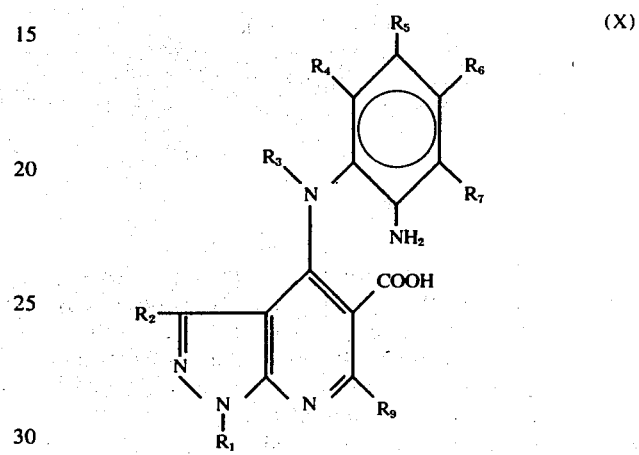

which is cyclized to the compound of formula I by reacting with an inorganic acid chloride like thionyl chloride, phosphorus trichloride or the like.

Compounds of formula I may also be produced by an alternative route.

The compound of formula VI may be treated with an alkylating agent, e.g., an alkyl halide like ethyl iodide, to form an intermediate of the formula

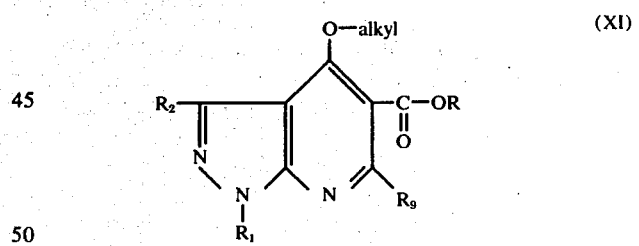

Saponification of the product of formula XI, e.g., with a conventional base, for example an alkali metal hydroxide, like potassium hydroxide or sodium hydroxide, produces a compound of the formula

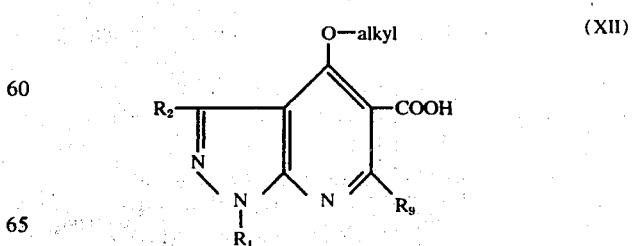

This acid is transformed to a product of the formula

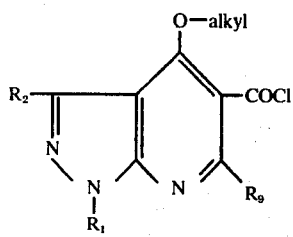

by treatment with an inorganic acid chloride like thionyl chloride.

Treatment of the compound of formula XIII with an appropriately substituted 2-nitroaniline in the presence of a base like pyridine, triethylmine or the like produces a compound of the formula

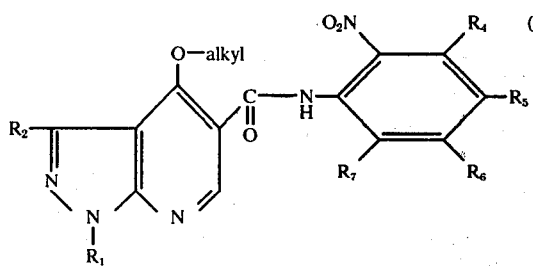

Catalytic reduction of the product of formula XIV in the presence of a catalyst like palladium on charcoal gives a compound of the formula

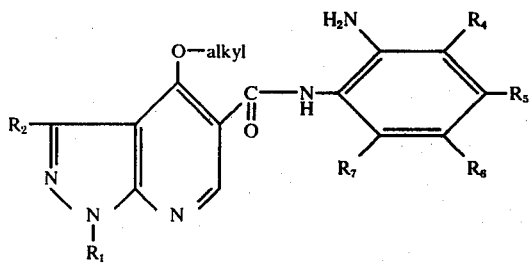

The compound of formula I is now produced by heating the compound of formula XV in a solvent like diethyleneglycol dimethyl ether, dimethylformamide or the like at a temperature of about 140°–160°.

A product of formula I wherein $R_1$ is hydrogen is produced by a modification of the foregoing procedure. According to this modification, a 5-aminopyrazole of formula II is used, wherein $R_1$ is an arylmethyl- or a heteromethyl group. This starting material has the formula

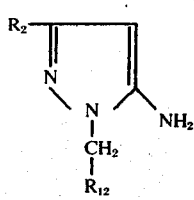

wherein $R_{12}$ is an aromatic or heterocyclic nucleus like phenyl, naphthyl, furyl, pyridyl, pyrimidyl, pyrazinyl or the like.

This material is processed as described above through the reaction with a compound of formula IV and cyclization of the product corresponding to formula V to obtain a compound of formula VI.

At this point, the compound of formula VI, having the $-CH_2-R_{12}$ substituent in the 1-position, is oxidized with an oxidizing agent like selenium dioxide in a high boiling solvent like diethyleneglycol dimethylether at about 160° C. This yields a compound of formula VI, wherein $R_1$ is hydrogen. Subsequently, this intermediate is converted to the chlorine compound of formula VII by means of phosphorus oxychloride which is processed as described above.

Compounds of formula I wherein $R_3$ is hydrogen and $R_8$ is other than hydrogen are now produced by reaction of a material of formula I with an appropriately substituted alkyl halide in the presence of sodium hydride. These derivatives have the formula

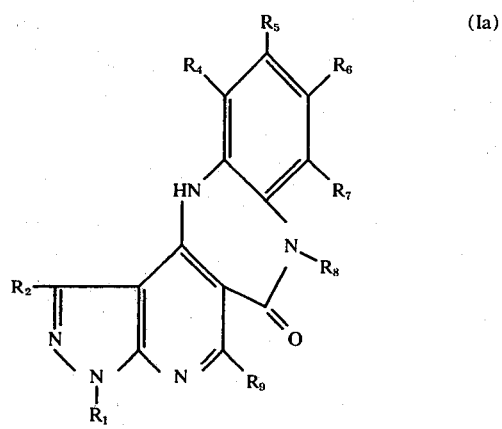

Compounds of formula I wherein $R_3$ and $R_8$ are other than hydrogen are produced by repeated reaction of the compound of formula I with the corresponding alkyl halide as described above.

The basic members of the group of formula I form salts which are also part of this invention. The salts include acid addition salts and quaternary ammonium salts, particularly the non-toxic, physiologically acceptable members. The bases of formula I form salts by reaction with a variety of inorganic and organic acids providing acid addition salts including, for example, hydrohalides (especially hydrochloride and hydrobromide), sulfate, nitrate, borate, phosphate, oxalate, tartrate, malate, citrate, acetate, ascorbate, succinate, benzenesulfonate, methanesulfonate, cyclohexanesulfamate and toluenesulfonate. The acid addition salts frequently provide a means for isolating the product, e.g., by forming and precipitating the salt in an appropriate menstruum in which the salt is insoluble, then after separation of the salt, neutralizing with a base such as barium hydroxide or sodium hydroxide, to obtain the free base of formula I. Other salts may then be formed from the free base by reaction with an equivalent of acid.

Quaternary ammonium salts include, for example, the lower alkyl halides and sulfates (e.g., methyl bromide and diethyl sulfate) and the phenyl-(lower alkyl) halides, sulfates and sulfonates (e.g., benzyl chloride, benzyl sulfate, benzenesulfonate and the like, which are formed by a conventional quaternization reaction.

The new compounds of this invention are central nervous system depressants and may be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-toxic, physiologically acceptable acid addition or quaternary ammonium salt thereof, may be administered orally or parenterally in a conventional dosage form such as tablet, capsule, injectable or the like. A single dose, or preferably 2 to 4 divided daily doses, provided on a basis of about 5 to 40 mg. per kilogram per day, preferably about 5 to 15 mg. per kilogram per day, is appropriate. These may be conventionally formulated in an oral or parenteral dosage form by compounding about 10 to 250 mg. per unit of dosage with conventional vehicle, excipient, binder, preservative, stabilizer, flavor or the like as called for by accepted pharmaceutical practice.

The new compounds also increase the intracellular concentration of adenosine-3',5'-cyclic monophosphate, and thus by the administration of about 1 to 50 mg/kg/day, preferably about 10 to 50 mg/kg, in single or two to four divided doses in conventional oral or parenteral dosage forms such as those described above may be used to alleviate the symptoms of asthma.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 15 to 50 mg/kg/day, preferably 15 to 25 mg/kg/day, in single or 2 to 4 divided doses, as indicated by the carageenan edema assay in rats. The active substance may be utilized in compositions such as tablets, capsules, solutions or suspensions containing up to about 300 mg. per unit of dosage of a compound or mixture of compounds of formula I or physiologically acceptable acid addition or quaternary ammonium salt thereof. They may be compounded in conventional manner with a physiologically acceptable vehicle or carrier, excipient, binder, preservative, stabilizer, flavor, etc. as called for by accepted pharmaceutical practice. Topical preparations containing about 0.1 to 3 percent by weight of active substance in a lotion, salve or cream may also be used.

The following examples are illustrative of the invention. All temperatures are on the centigrade scale.

EXAMPLE 1

1-ethyl-9-(3-dimethylamino)propyl-1H,4H-pyrazolo[3',4'-2,3]pyrido[4,5-e]b-benzo-1,5-diazepin-9H-10-one a. [[(1-Ethyl-5-pyrazolyl)amino]methylene]malonic acid diethyl ester 245 g. of 1-Ethyl-5-aminopyrazole (2.2 mol.) and 476 g. of ethoxymethylene malonic acid diethyl ester (2.2 mol.) are heated to 120° (bath temperature) for 2 hours with stirring. The ethanol formed by this reaction is removed by means of a water aspirator. Then vacuum distillation (b.p.$_{0.1}$ 154°–160°) yields 520 g. (84% of theory) of a quickly crystallizing oil [[(1-ethyl-5-pyrazolyl)amino]methylene]malonic acid diethyl ester, m.p. 50°–53°.

The compound is recrystallized from N-hexane, m.p. 55°–57°.

The hydrochloride salt is formed by treating the above product with dilute ethanolic hydrogen chloride solution.

b. 1-Ethyl-4-hydroxy-1H-pyrazolo[3,4b]-pyridine-5-carboxylic acid ethyl ester 253 g. of [[(1-Ethyl-5-pyrazolyl)amino]methylene]-malonic acid diethyl ester (0.09 mol.) are dissolved in 770 g. of diphenyl ether. The reaction mixture is heated to 235°–250° (bath temperature) and allowed to react at this temperature for 1–2 hours while the resulting ethanol is continuously distilled off. The last amount of alcohol is removed by means of a water aspirator. The diphenyl ether is separated by distillation with a fractionating column in vacuo. The 1-ethyl-4-hydroxy-1H-pyrazolo[3,4-b]pyridine-5-carboxylic acid ethyl ester is obtained at b.p.$_{0.05}$ 115°–120°, yield 195 g.= 92% of theory, m.p. 85°–87°. The compound is recrystallized from benzene (90° to 100°), m.p. 87°–89°.

c. 4-Chloro-1-ethyl-1H-pyrazolo[3,4-b]pyridine-5-carboxylic acid ethyl ester

A mixture of 23.5 g. of 1-ethyl-4-hydroxy-1H-pyrazolo[3,4-b]pyridine-5-carboxylic acid ethyl ester (0.1 mol.) and 150 ml. of phosphorus oxychloride is refluxed for 4 hours. Subsequently, the excess phosphorus oxychloride is removed by means of vacuum distillation. As soon as the phosphorus oxychloride has been removed, the oily residue solidifies on cooling. It is treated with water and filtered under suction (24.5 g.), m.p. 55°–60°. The 4-chloro-1-ethyl-1H-pyrazolo[3,4-b]-pyridine-5-carboxylic acid ethyl ester is recrystallized from N-hexane (22.5 g. = 87%), m.p. 62°.

d. 4-[(2-aminophenyl)amino]-1-ethyl-1H-pyrazolo[3,4-b]pyridine-5-carboxylic acid ethyl ester 253 g. of 4-Chloro-1-ethyl-1H-pyrazolo[3,4-b]pyridine-5-carboxylic acid ethyl ester (1 mol.) and 108 g. of o-phenylenediamine (1 mol.) are dissolved in 750 ml. of diethyleneglycol dimethyl ether, 150 g. of triethylamine are added and the mixture is refluxed for 5 hours. After this time the solution is cooled to room temperature and diluted with 1 liter of water. 4-[(2-aminophenyl)amino]-1-ethyl-1H-pyrazolo[3,4-b]pyridine-5-carboxylic acid ethyl ester solidifies and is recrystallized from methanol. Yield 280 g. (86%), m.p. 126°–128°.

e. 1-Ethyl-1H,4H-pyrazolo[3',4'-2,3]pyrido[4,5-e]b-benzo-1,5-diazepin-(9H)-10-one 162.5 g. of 4-[(2-aminophenyl)amino]-1-ethyl-1H-pyrazolo[3,4-b]pyridine-5-carboxylic acid ethyl ester (0.5 mol.) are suspended in 1 liter of anhydrous o-xylene and refluxed for 5 hours with 56 g. of potassium tert. butylate. After this time, the reaction mixture is cooled to room temperature and acidified with acetic acid. 1-Ethyl-1H,4H-pyrazolo[3',4'-2,3]-pyrido[4,5-e]b-benzo-1,5-diazepin-(9H)-10-one crystallizes and is filtered and treated with water. Recrystallization from acetic acid yields 99 g. of yellow crystals (71%), m.p. 298°–300°.

f. 1-Ethyl-9-[(3-dimethylamino)propyl]-1H,4H-pyrazolo[3',4'-2,3]pyrido[4,5-e]b-benzo-1,5-diazepin-(9H)-10-one 2.8 g. of 1Ethyl-1H,4H-pyrazolo[3',4'-2,3]pyrido[4,5-e]b-benzo-1,5-diazepin-(9H)-10-one (0.01 mol.) is continuously added to a refluxing suspension of 0.48 g. of sodium hydride (0.02 mol.) in 50 ml. of anhydrous dioxane. The mixture is refluxed for 30 minutes. After this time, 1.4 g. of 3-dimethylaminopropyl chloride (0.11 mol.) dissolved in 10 ml. of dioxane are dropped into the reaction mixture over a period of 2 hours. The resulting red solution is refluxed for an additional 10 hours. The mixture is filtered hot and evaporated to dryness. A yellow oil remains, which is dissolved in about 50 ml. of chloroform and acidified with a few drops of acetic acid. Sodium acetate precipitates on standing and is filtered off. The chloroform solution is evaporated and the oily residue crystallizes on the addition of 50 ml. of ether. Recrystallization from ethyl acetate yeilds 2.8 g. of 1-ethyl-9-[(3-dimethylamino)propyl]-1H,4H-pyrazolo[3',4'-2,3]pyrido[4,5-e]b-benzo-1,5-diazepin-(9H)-10-one (77%), m.p. 71°–73°.

Example 2

1,4-Diethyl-9-methyl-1H,4H-pyrazolo[3',4'-2,3]pyrido[4,5-e]b-benzo-1,5-diazepin-(9H)-10-one a. 1-Ethyl-9-methyl-1H,4H-pyrazolo[3',4'-2,3]-pyrido[4,5-e]b-benzo-1,5-diazepin-(9H)-10-one 5.6 g. of 1-Ethyl-1H,4H-pyrazolo[3',4'-2,3]pyrido[4,5-e]b-benzo-1,5-diazepin-(9H)-10-one (0.02 mol.) are added to a refluxing suspension of 0.06 g. of sodium hydride (0.024 mol.) in 50 ml. of anhydrous dioxane. The mixture is refluxed for 30 minutes. After this time 2.85 g. of methyl iodide dissolved in 10 ml. of dioxane are added over a period of 2 hours. The mixture is refluxed for an additional 8 hours. After cooling, the precipitated sodium iodide is filtered off and the filtrate is evaporated to dryness. The oily residue crystallizes on addition of methyl alcohol and yields on recrystallization from ethyl acetate/petroleum ether 4.9 g. of 1-ethyl-9-methyl-1H,4H-pyrazolo[3',4'-2,3]pyrido[4,5-e]b-benzo-1,5-diazepin-(9H)-10-one (84%), m.p. 192°–194°.

b. 1,4-Diethyl-9-methyl-1H,4H-pyrazolo[3',4'-2,3]-pyrido[4,5-e]b-benzo-1,5-diazepin-(9H)-10-one 2.9 g. of 1-Ethyl-9-methyl-1H,4H-pyrazolo[3',4'-2,3]pyrido[4,5-e]b-benzo-1,5-diazepin-(9H)-10-one (0.01 mol.) are added to a refluxing suspension of 0.48 g. of sodium hydride (0.02 mol.) in dioxane. The temperature is maintained for an additional 30 minutes. then 3.1 g. of ethyl iodide in 10 ml. of dioxane are added over a period of 3 hours. Refluxing is continued for 10 hours. The precipitated sodium iodide is filtered off and the residue evaporated to dryness. On addition of methanol, 1,4-diethyl-9-methyl-1H,9H-pyrazolo[3',-4'-2,3]pyrido[4,5-e]b-benzo-1,5-diazepin-(9H)-10-one crystallizes. Recrystallization from ethyl acetate/petroleum ether yields 2.9 g. (90%), m.p. 150°–152°.

EXAMPLE 3

1.9-Diethyl-1H,4H-pyrazolo[3',4'-2,3]pyrido[4,5-e]b-benzo-1,5-diazepin-(9H)-10-one a. 4-[[(2-ethylamino)phenyl]amino]-1-ethyl-1H-pyrazolo[3,4-b]pyridine-5-carboxylic acid ethyl ester 4-[[(2-amino)phenyl]amino]-1-ethyl-1H-pyrazolo[3,4-b]pyridine-5-carboxylic acid ethyl ester (0.1 mol.), 21 g. of potassium carbonate (0.15 mol.) and 23.5 g. of ethyl iodide (0.15 mol.) are heated with stirring for 15 hours at 80° in 100 ml. of dimethylformamide. After that time, the mixture is filtered hot and 100 ml. of water are added. 4-[[(2-ethylamino)phenyl]amino]-1-ethyl-1H-pyrazolo[3,4-b]pyridine-5-carboxylic acid ethyl ester precipitates, is filtered and recrystallized from alcohol, yield 25 g. (71%) m.p. 147°–152°.

b. 4-[[(2-ethylamino)phenyl]amino]-1-ethyl-1H-pyrazolo[3,4-b]pyridine-5-carboxylic acid 3.5 g. of 4-[[(2-ethylamino)phenyl]amino]-1-ethyl-1H-pyrazolo[3,4-b]pyridine-5-carboxylic acid ethyl ester (0.01 mol.) are heated at 60° for 12 hours with a solution of 1.7 g. of potassium hydroxide in 50 ml. of alcohol. The solvent is distilled off and the residue is dissolved in about 100 ml. of water. On acidifying with acetic acid, 4-[[(2-ethylamino)phenyl]amino]-1-ethyl-1H-pyrazolo[3,4-b]pyridine-5-carboxylic acid crystallizes and is purified by recrystallization from acetic acid, yeild 2.8 g. (93%), m.p. 224°–226°.

c. 1.9-Diethyl-1H,4H-pyrazolo[3',4'-2,3]pyrido[4,5-e]b-benzo-1,5-diazepin-(9H)-10-one 2.25 g. of 4-[[(2-ethylamino)phenyl]amino]-1-ethyl-1H-pyrazolo[3,4-b]pyridine-5-carboxylic acid (0.01 mol.) are added to 15 ml. of thionyl chloride and refluxed for 6 hours. The excess thionyl chloride is removed in vacuo and the residue treated with water. 1,9-Diethyl-1H,4H-pyrazolo[3',4'-2,3]pyrido[4,5-e]b-benzo-1,5-diazepin-(9H)-10-one precipitates and is recrystallized from methanol, yield 2.2 g. (70%), m.p. 258°–260°.

EXAMPLE 4

7-Chloro-1-ethyl-1H,4H-pyrazolo[3',4'-2,3]pyrido[4,5-e]b-benzo-1,5-diazepin-(9H)-10-one a. 4-[[(2-nitro-4-chloro)phenyl]amino]-1-ethyl-1H-pyrazolo-[3,4-b]pyridine-5-carboxylic acid ethyl ester 253 g. of 1-Ethyl-4-chloro-1H-pyrazolo[3,4-b]pyridine-5-carboxylic acid ethyl ester (1 mol.), 24 g. of sodium hydride (1 mol.) and 172 g. of 2-nitro-4-chloroaniline (1 mol.) are heated together in 1.5 liter of anhydrous dioxane for 10 hours. After this time, the mixture is acidified with acetic acid. 4-[[(2-nitro-4-chloro)phenyl]amino]-1-ethyl-1H-pyrazolo[3,4-b]pyridine-5-carboxylic acid ethyl ester precipitates and is filtered after cooling. Recrystallization from methanol yields 320 g. (83%), m.p. 192°–193°.

b. 4-[[(2-amino-4-chloro)phenyl]amino]-1-ethyl-1H-pyrazolo[3,4-b]pyridine-5-carboxylic acid ethyl ester 38.9 g. of 4-[[(2-nitro-4-chloro)phenyl]amino]-1-ethyl-1H-pyrazolo[3,4-b]-pyridine-5-carboxylic acid ethyl ester are dissolved in 100 ml. of acetic acid at 50°. The mixture is hydrogenated with 0.5 g. of palladium on charcoal until the theoretical amount of hydrogen has been absorbed. The catalyst is filtered off and the solvent removed in vacuo. The oily residue of 4-[[(2- amino-4-chloro)phenyl]amino]-1-ethyl-1H-pyrazolo[3,4-b]pyridine-5-carboxylic acid ethyl ester crystallizes after the addition of about 50 ml. of water. Recrystallization from methanol/water yields 20 g. (57%), m.p. 195°–198°.

c. 7-Chloro-1-ethyl-1H,4H-pyrazolo[3',4'-2,3]pyrido[4,5-e]b-benzo-1,5-diazepin-(9H)-10-one 3.6 g. of 4-[[(2-amino-4-chloro]phenyl]amino-1-ethyl-1H-pyrazolo[3,4-b]pyridine-5-carboxylic acid ethyl ester (0.01 mol.) are suspended in 20 ml. of anhydrous o-xylene and refluxed for 5 hours with 1.5 g. of potassium-t-butylate. After this time, the reaction mixture is cooled to room temperature and acidified with acetic acid. 7-Chloro-1-ethyl-1H,4H-pyrazolo[3',4'-2,3]pyrido[4,5-e]b-benzo-1,5-diazepin-(9H)-10-one precipitates and is recrystallized from acetic acid, yield 2.1 g. (67%), m.p. 285°–288°.

EXAMPLE 5

6-Chloro-1,4,9-triethyl-1H,4H-pyrazolo[3',4'-2,3]pyrido[4,5-e]-b-benzo-1,5-diazepin-(9H)-10-one a. 4-Ethoxy-1-ethyl-1H-pyrazolo[3,4-b]pyridine-5-carboxylic acid ethyl ester In a solution of 259 g. (1.1 mol.) of 1-ethyl-4-hydroxy-1H-pyrazolo[3,4-b]pyridine-5-carboxylic acid ethyl ester in 1700 ml. of dimethylformamide, 400 g. of well powdered potassium carbonate and 300 g. of ethyl iodide are introduced. The reaction mixture is stirred for 7 hours at 65° and filtered under suction, while hot, from excess potassium carbonate. Upon standing overnight, 165 g. of 4-ethoxy-1-ethyl-1H-pyrazolo[3,4-b]pyridine-5-carboxylic acid ethyl ester crystallize out of the solution, m.p. 112°–115°. After evaporation of the mother liquor, an additional 80 g. are obtained. The total yield amounts to 85% of theory. The compound is recrystallized from benzene (90°–100°), m.p. 113°–115°.

b. 4-Ethoxy-1-ethyl-1H-pyrazolo[3,4-b]pyridine-5-carboxylic acid 263 g. of 4-Ethoxy-1-ethyl-1H-pyrazolo[3,4-b]pyridine-5-carboxylic acid ethyl ester (1 mol.) are heated with a solution of 114 g. of potassium hydroxide (2 mol.) in 1 liter of ethanol at 60° for 12 hours. After this time, the solvent is removed in vacuo and the residue is dissolved in 1.5 liters of water. After acidifying with acetic acid, 4-ethoxy-1-ethyl-1H-pyrazolo[3,4-b]pyridine-5-carboxylic acid precipitates. Recrystallization from alcohol yields 215 g. (91%), m.p. 198°–199°.

c. 4-Ethoxy-1-ethyl-1H-pyrazolo[3,4-b]pyridine-5-carboxylic acid chloride 117.5 g. of 4-ethoxy-1-ethyl-1H-pyrazolo[3,4-b]pyridine-5-carboxylic acid (0.5 mol.) are slowly added with stirring to 300 ml. of thionyl chloride. The mixture is refluxed for 4 hours, excess thionyl chloride is removed in vacuo and the residue dissolved in 500 ml. anhydrous diethylether. The undissolved material is filtered off and the filtrate intensively cooled. The acid chloride precipitates; it is filtered under suction and washed well with cold water. Yield 105 g. (80%), m.p. 72°–73°.

d. 4-Ethoxy-1-ethyl-1H-pyrazolo[3,4-b]pyridine-5-(2'-nitro-4'-chloro)carboxanilide 25.3 g. of 4-ethoxy-1-ethyl-1H-pyrazolo[3,4-b]pyridine-5-carboxylic acid chloride (0.1 mol.), 16.8 g. of 2-nitro-4-chloroaniline and 20.2 g. of triethylamine (0.2 mol.) are heated under reflux in 500 ml. of dry o-xylene for 5 hours. After this time, the precipitated triethylamine hydrochloride is filtered hot and the filtrate cooled in an ice-bath. 4-Ethoxy-1-ethyl-1H-pyrazolo[3,4-b]pyridine-5-(2-nitro-4-chloro)carboxanilide crystallizes and is recrystallized from dimethylformamide. Yield 31.5 g. (80%), m.p. 210–212°.

e. 4-Ethoxy-1-ethyl-1H-pyrazolo[3,4-b]pyridine-5-(2-amino-4-chloro)carboxanilide 3.9 g. of 4-Ethoxy-1-ethyl-1H-pyrazolo[3,4-b]pyridine-5-(2'-nitro-4'-chloro)carboxanilide (0.01 mol.) are added to a suspension of 0.1 g. of palladium on charcoal in 50 ml. of acetic acid. The mixture is hydrogenated, until the theoretical amount of hydrogen is absorbed. The catalyst is filtered off and the filtrate evaporated to dryness. Recrystallization of the residue yields 3.1 g. of 4-ethoxy-1-ethyl-1H-pyrazolo[3,4-b]pyridine-5-(2-amino-4-chloro)carboxanilide (86%), m.p. 302°–303°.

f. 6-Chloro-1-ethyl-1H,4H-pyrazolo[3',4'-2,3]pyrido[4,5-e]b-benzo-1,5-diazepin(9H)-10-one 3.6 g. of 4-ethoxy-1-ethyl-1H-pyrazolo[3,4-b]pyridine-5-(2-amino-4-chloro)carboxanilide (0.01 mol.) are heated in 100 ml. of dimethylformamide for 24 hours. After this time, the solvent is distilled off and the residue recrystallized from butyl alcohol. Yield 2 g. (65%), m.p. 232°–234°.

g. 6-Chloro-1,4,9-triethyl-1H,4H-pyrazolo[3',4'-2,3]pyrido[4,5-e]b-benzo-1,5-diazepin-(9H)-10-one 3.1 g. of 6-chloro-1-ethyl-1H,4H-pyrazolo[3',4'-2,3]-pyrido[4,5-e]b-benzo-1,5-diazepine-(9H)-10-one (0.01 mol.) are suspended in 50 ml. of dry dioxane. 0.036 g. of sodium hydride (0.015 mol.) are added and the mixture is refluxed for half an hour. Then 4.6 g. of ethyl iodide (0.03 mol.) dissolved in 10 ml. of dioxane are dropped in over a period of 3 hours with continuous stirring. Reflux and stirring are continued for 10 hours. The precipitated sodium iodide is filtered, the filtrate acidified with acetic acid and evaporated to dryness. Addition of 10 ml. of methyl alcohol yields crystalline 6-chloro-1,4,9-triethyl-1H,4H-pyrazolo[3',4'-2,3]pyrido[4,5-e]b-benzo-1,5-diazepin-(9H)-10-one. Yield 3 g. (81%), m.p. 174°–176°.

The following additional compounds are produced by the procedure of Example 1:

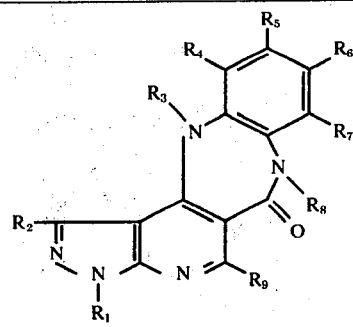

| Ex. | R₁ | R₂ | R₃ | R₄ | R₅ | R₆ | R₇ | R₈ | R₉ | m.p. |
|---|---|---|---|---|---|---|---|---|---|---|
| 6 | $C_2H_5$ | H | H | H | H | H | H | $-(CH_2)_2N(CH_3)_2$ | H | 223–225° |
| 7 | $C_2H_5$ | H | H | H | H | H | H | $-CH(CH_3)CH_2N(CH_3)_2$ | H | 115° |
| 8 | $C_2H_5$ | H | $-(CH_2)_3N(CH_3)_2$ | H | H | H | H | $-C_2H_5$ | H | 108–110° |
| 9 | $C_2H_5$ | H | H | H | H | H | H | $-(CH_2)_2N(C_2H_5)_2$ | H | 212–214° |
| 10 | $C_2H_5$ | H | H | H | H | H | H | $-(CH_2)_3N^+(CH_3)_3 I^-$ | H | 264–265° |
| 11 | $C_2H_5$ | H | H | H | H | H | H | $-(CH_2)_3N\text{(piperidine)}$ | H | 174–175° |
| 12 | $C_2H_5$ | H | $-(CH_2)_3N(CH_3)_2$ | H | H | H | H | $-CH_3$ | H | oil |
| 13 | phenyl | $C_2H_5$ | $CH_3$ | H | H | $CH_3$ | H | $-(CH_2)_2N(C_2H_5)_2$ | $CH_3$ | |
| 14 | phenyl | H | $C_2H_2$ | H | H | H | H | $-(CH_2)_2N(C_2H_5)_2$ | H | |
| 15 | cyclopentyl | H | $C_2H_5$ | H | H | H | $CH_3$ | $-(CH_2)_3N(CH_3)_2$ | H | |
| 16 | cyclohexyl | $CH_3$ | $-(CH_2)_3N(CH_3)_2$ | H | H | Cl | H | $C_2H_5$ | $C_2H_5$ | |
| 17 | $C_2H_5$ | phenyl | $-CH_2$-phenyl | H | H | $C_2H_5$ | H | $-(CH_2)_2N(CH_3)_2$ | H | |
| 18 | $C_2H_5$ | H | $C_2H_5$ | H | H | H | H | $-(CH_2)_2NH_2$ | H | |
| 19 | H | $CH_3$ | $-(CH_2)_2NH_2$ | H | H | H | H | $-(CH_2)_2NH_2$ | H | |
| 20 | $C_2H_5$ | H | $-(CH_2)_2N\text{(piperidine)}$ | H | H | H | H | $C_2H_5$ | H | |
| 21 | $C_2H_5$ | H | $-(CH_2)_3N\text{(N-methylpiperazine)}$ | H | $CH_3$ | H | H | $C_2H_5$ | H | |
| 22 | $C_2H_5$ | H | H | H | H | H | H | $-(CH_2)_2N\text{(piperidine)}$ | H | |
| 23 | $CH_3$ | H | H | H | Cl | Cl | H | $-(CH_2)_2N(CH_3)_2$ | H | |
| 24 | $C_2H_5$ | $CH_3$ | $-(CH_2)_2N(C_2H_5)_2$ | H | H | $OCH_3$ | H | $C_2H_5$ | H | |

-continued

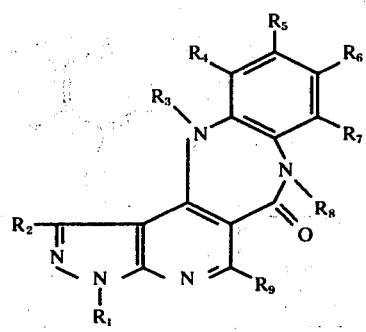

| Ex. | R₁ | R₂ | R₃ | R₄ | R₅ | R₆ | R₇ | R₈ | R₉ | m.p. |
|---|---|---|---|---|---|---|---|---|---|---|
| 25 | $C_2H_5$ | H | —(CH₂)₂N⟨pyrrolidine-OCH₃⟩ | H | H | H | H | $C_2H_5$ | H | |
| 26 | Ph—CH₂— | H | H | H | H | H | H | —(CH₂)₃N⟨thiomorpholine⟩ | H | |
| 27 | $C_2H_5$ | H | —(CH₂)₂N⟨CH₃-thiomorpholine⟩ | $OCH_3$ | H | H | $OCH_3$ | H | H | |
| 28 | $C_2H_5$ | $CH_3$ | —(CH₂)₃N(CH₃)₂ | H | H | Cl | H | $CH_3$ | Ph | |
| 29 | $C_2H_5$ | H | —(CH₂)₂NH(CH₂CH₂OH) | H | H | H | H | $C_2H_5$ | H | |
| 30 | $C_2H_5$ | H | —(CH₂)₃N(CH₂CH₂OH)₂ | H | H | H | H | $C_2H_5$ | H | |
| 31 | $C_2H_5$ | H | $CH_3$ | H | H | H | H | —(CH₂)₂NH(CH₂CH₂OH) | H | |
| 32 | $C_2H_5$ | H | —CH₂N⟨piperazine⟩N—C₂H₄OH | H | H | H | H | $CH_3$ | H | |
| 33 | cyclohexyl | H | $C_2H_5$ | H | H | H | H | —(CH₂)₃NHC₂H₅ | $CH_3$ | |
| 34 | $C_2H_5$ | H | —CH₂N⟨morpholine⟩ | H | H | H | H | $C_2H_5$ | H | |
| 35 | Ph—CH₂ | $CH_3$ | $C_3H_7$ | H | H | H | H | $CH_3$ | H | |

The following additional examples are produced by the procedure of Examples 2, 3 or 4;

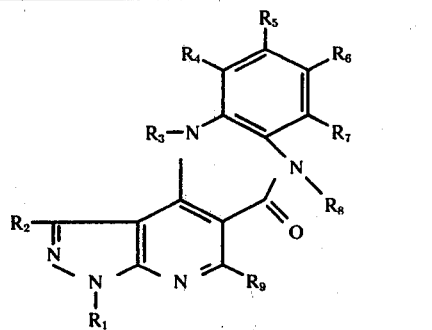

| Ex. | $R_1$ | $R_2$ | $R_3$ | $R_4$ | $R_5$ | $R_6$ | $R_7$ | $R_8$ | $R_9$ | m.p. |
|---|---|---|---|---|---|---|---|---|---|---|
| 36 | $C_2H_5$ | H | $C_2H_5$ | H | H | H | H | $C_2H_5$ | H | 142–144° |
| 37 | $C_2H_5$ | H | H | H | H | H | H | $-(CH_2)_3CH_3$ | H | 202–205° |
| 38 | $C_2H_5$ | H | $CH_3$ | H | H | H | H | $CH_3$ | H | 210–211° |
| 39 | $C_2H_5$ | H | H | H | H | H | H | $CH_3$ | H | 195–197° |
| 40 | $C_2H_5$ | H | $-(CH_2)_9CH_3$ | H | H | H | H | $-(CH_2)_9CH_3$ | H | 46–47° |
| 41 | $C_2H_5$ | H | $-CH_2-\text{C}_6H_5$ | H | H | H | H | $-CH_2-\text{C}_6H_5$ | H | 186–187° |
| 42 | $C_2H_5$ | H | $-(CH_2)_3CH_3$ | H | H | H | H | $-(CH_2)_3CH_3$ | H | 87–89° |
| 43 | $C_2H_5$ | H | $C_2H_5$ | H | H | Cl | H | $C_2H_5$ | H | 156–158° |
| 44 | $C_2H_5$ | H | $C_2H_5$ | H | H | Cl | H | $C_4H_9$ | H |  |
| 45 | $C_2H_5$ | $CH_3$ | cyclohexyl | H | H | Cl | H | $C_2H_5$ | H |  |
| 46 | $C_2H_5$ | H | cyclohexyl | H | H | H | H | cyclohexyl | H |  |
| 47 | H | H | $CH_3$ | H | H | H | H | $CH_3$ | $CH_3$ |  |
| 48 | $C_2H_5$ | $CH_3$ | H | H | H | H | H | H | H |  |
| 49 | $C_2H_5$ | H | $CH_3$ | H | H | $OCH_3$ | H | H | $CH_3$ |  |
| 50 | $C_2H_5$ | H | $C_2H_5$ | H | H | $OCH_3$ | H | H | $C_2H_5$ |  |

The following compounds are prepared by the procedure of Example 5:

| Ex. | $R_1$ | $R_2$ | $R_3$ | $R_4$ | $R_5$ | $R_6$ | $R_7$ | $R_8$ | $R_9$ |
|---|---|---|---|---|---|---|---|---|---|
| 51 | $C_2H_5$ | H | $CH_3$ | H | Cl | H | H | $CH_3$ | H |
| 52 | $C_2H_5$ | H | $CH_2CH_2N(CH_3)_2$ | H | Cl | H | H | $CH_3$ | H |
| 53 | $C_2H_5$ | H | $-(CH_2)_3N\text{-piperidino}$ | H | $OCH_3$ | H | H | $CH_3$ | H |
| 54 | $C_2H_5$ | H | $-(CH_2)_3N(CH_3)_2$ | Cl | Cl | H | H | $(CH_2)_3N(CH_3)_2$ | H |
| 55 | $C_2H_5$ | $CH_3$ | H | $OCH_3$ | Cl | H | H | $CH_3$ | H |
| 56 | $C_2H_5$ | $CH_3$ | H | H | $OCH_3$ | H | H | $(CH_2)_3N\text{-piperidino}$ | H |
| 57 | $C_2H_5$ | H | $-C_3H_7$ | $CH_3$ | Cl | H | H | $C_2H_5$ | $CH_3$ |
| 58 | $C_2H_5$ | H | cyclohexyl | Cl | H | H | H | $CH_3$ | $CH_3$ |

What is claimed is:
1. A compound of the formula

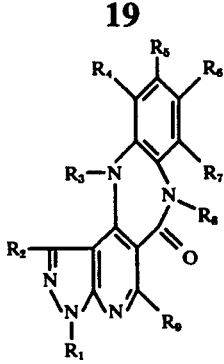

wherein $R_1$ is hydrogen, lower alkyl, phenyl, phenyl-lower alkyl or $C_3$ to $C_6$ cyclo-lower alkyl; $R_2$ is hydrogen, lower alkyl or phenyl; $R_3$ and $R_8$ each is hydrogen, alkyl up to 10 carbon atoms, phenyl-lower alkyl, $C_3$ to $C_6$ cyclo-lower alkyl or

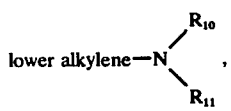

wherein $R_{10}$ and $R_{11}$ each is hydrogen, lower alkyl or hydroxy-lower alkyl or the

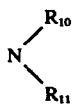

radical forms the heterocyclic pyrrolidino, piperidino, morpholino, thiamorpholino, (lower alkoxy)-piperidino, (lower alkyl)piperidino, (lower alkyl)pyrrolidino, (lower alkoxy)pyrrolidino, (lower alkyl)morpholino, (lower alkoxy)morpholino, (lower alkyl) thiamorpholino or (lower alkoxy)thiamorpholino $R_4$, $R_5$, $R_6$ and $R_7$ each is hydrogen, halogen, lower alkyl or lower alkoxy; and $R_9$ is hydrogen, lower alkyl or phenyl; and physiologically acceptable acid addition salts and quaternary lower alkyl halide, lower alkyl sulfate, phenyl-lower alkyl halide, phenyl-lower alkyl sulfate, lower alkyl sulfonate and phenylsulfonate salts thereof.

2. A compound of the formula

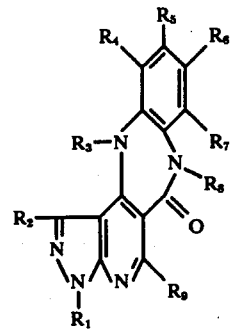

wherein $R_1$ is hydrogen or lower alkyl; $R_2$ is hydrogen or methyl; $R_3$ and $R_8$ each is hydrogen, lower alkyl or di(lower alkyl)amino-lower alkylene; $R_4$, $R_5$, $R_6$, $R_7$ are hydrogen, halogen or lower alkoxy; $R_9$ is hydrogen or lower alkyl and physiologically acceptable acid addition salts thereof.

3. A compound as in claim 2 wherein $R_1$ is ethyl; $R_2$ is hydrogen or methyl; $R_3$ and $R_8$ each is ethyl or dimethylaminopropyl; $R_4$, $R_5$, $R_6$ and $R_7$ are hydrogen, chlorine or methoxy; and $R_9$ is hydrogen.

4. A compound as in claim 1 wherein $R_1$ is lower alkyl and $R_8$ is di(lower alkyl)amino-lower alkylene.

5. A compound as in claim 1 wherein $R_1$, $R_3$ and $R_8$ each is lower alkyl.

6. A compound as in claim 2 wherein $R_1$ and $R_8$ each is lower alkyl.

7. A compound as in claim 2 wherein $R_1$ is lower alkyl and $R_6$ is halogen.

8. A compound as in claim 2 wherein $R_1$ is lower alkyl, $R_2$, $R_3$, $R_4$, $R_5$, $R_6$, $R_7$ and $R_9$ each is hydrogen and $R_8$ is di(lower alkyl)amino-lower alkylene.

9. A compound as in claim 8 wherein $R_1$ is ethyl and $R_8$ is dimethylaminopropyl.

10. A compound as in claim 2 wherein $R_1$, $R_3$ and $R_8$ each is lower alkyl, and $R_2$, $R_4$, $R_5$, $R_6$, $R_7$ and $R_9$ each is hydrogen 11. A compound as in claim 10 wherein $R_1$ and $R_3$ each is ethyl and $R_8$ is methyl.

12. A compound as in claim 2 wherein $R_1$ and $R_8$ each is lower alkyl, and $R_2$, $R_3$, $R_4$, $R_5$, $R_6$, $R_7$ and $R_9$ each is hydrogen.

13. A compound as in claim 12 wherein $R_1$ and $R_8$ each is ethyl.

14. A compound as in claim 2 wherein $R_1$ is lower alkyl, $R_2$, $R_3$, $R_4$, $R_5$, $R_7$, $R_8$ and $R_9$ each is hydrogen and $R_6$ is halogen.

15. A compound as in claim 14 wherein $R_1$ is ethyl and $R_6$ is chlorine.

* * * * *